US012594139B2

(12) United States Patent　　　　(10) Patent No.: US 12,594,139 B2
Morey et al.　　　　　　　　　　　(45) Date of Patent: Apr. 7, 2026

(54) DEVICES AND METHODS TO ACCESS A TARGET WITHIN THE BODY

(71) Applicant: Boston Scientific Medical Device Limited, Galway (IE)

(72) Inventors: Subodh Morey, Ponda (IN); Ashish Jain, Lucknow (IN); Timothy Paul Harrah, Cambridge, MA (US); Rajivkumar Singh, Thane (IN)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 567 days.

(21) Appl. No.: 17/890,774

(22) Filed: Aug. 18, 2022

(65) Prior Publication Data

US 2022/0401177 A1　　　Dec. 22, 2022

Related U.S. Application Data

(63) Continuation of application No. 16/640,566, filed as application No. PCT/US2018/048094 on Aug. 27, 2018, now Pat. No. 11,452,575.
(Continued)

(51) Int. Cl.
*A61B 90/11*　　　(2016.01)
*A61B 17/34*　　　(2006.01)
*A61B 90/00*　　　(2016.01)

(52) U.S. Cl.
CPC .......... *A61B 90/11* (2016.02); *A61B 17/3403* (2013.01); *A61B 2017/3407* (2013.01);
(Continued)

(58) Field of Classification Search
CPC ........ A61B 17/3403; A61B 2017/3429; A61B 2017/3407; A61B 90/11
See application file for complete search history.

(56) References Cited

U.S. PATENT DOCUMENTS 4,809,679 A * 3/1989 Shimonaka ....... A61M 39/0606
　　　　　　　　　　　　　　　　D24/129
4,886,502 A 12/1989 Poirier et al.
(Continued)

FOREIGN PATENT DOCUMENTS

DE 202008010644 U1 12/2009
EP 1649818 A2 4/2006
(Continued)

OTHER PUBLICATIONS

International Search Report and Written Opinion for the International Patent Application No. PCT/US2018/048094, dated Nov. 15, 2018, 11 pages.
(Continued)

*Primary Examiner* — Dianne Dornbusch
(74) *Attorney, Agent, or Firm* — Seager Tufte Wickhem LLP

(57) ABSTRACT

The present disclosure relates generally to the field of medical devices and establishing access to a target within the body, such as placing an access needle into a renal capsule into the human body. In particular, the present disclosure relates to devices and methods for performing a percutaneous nephrolithotomy (PCNL) procedure accurately and efficiently while minimizing exposure of the medical professional to harmful radiation.

20 Claims, 7 Drawing Sheets

Related U.S. Application Data

(60) Provisional application No. 62/551,121, filed on Aug. 28, 2017.

(52) U.S. Cl.
CPC ................. *A61B 2017/3429* (2013.01); *A61B 2090/3966* (2016.02)

(56) References Cited

U.S. PATENT DOCUMENTS

| | | | |
|---|---|---|---|
| 5,833,655 A | 11/1998 | Freed et al. | |
| 5,972,030 A | 10/1999 | Garrison et al. | |
| 6,689,142 B1 | 2/2004 | Tremaglio, Jr. et al. | |
| 7,999,145 B2 * | 8/2011 | Kairinos | A61F 13/05 |
| | | | 602/42 |
| 8,057,487 B2 | 11/2011 | Chu et al. | |
| 9,610,111 B2 | 4/2017 | Arthur et al. | |
| 9,968,373 B1 | 5/2018 | Greenhalgh et al. | |
| 2006/0052794 A1 * | 3/2006 | McGill | B01F 33/50112 |
| | | | 366/331 |
| 2011/0028797 A1 | 2/2011 | Yee et al. | |
| 2011/0184350 A1 | 7/2011 | McKay | |
| 2014/0257418 A1 * | 9/2014 | Arthur | A61B 50/20 |
| | | | 606/86 R |
| 2014/0277209 A1 * | 9/2014 | Arthur | A61B 17/8855 |
| | | | 606/86 R |
| 2014/0330277 A1 | 11/2014 | Ogrodnik et al. | |
| 2014/0364861 A1 | 12/2014 | Easter et al. | |
| 2018/0368862 A1 | 12/2018 | Jain et al. | |
| 2020/0352672 A1 | 11/2020 | Chu et al. | |
| 2021/0267609 A1 | 9/2021 | Nguyen et al. | |

FOREIGN PATENT DOCUMENTS

| | | |
|---|---|---|
| WO | 2011156701 A2 | 12/2011 |
| WO | 2019046158 A1 | 3/2019 |

OTHER PUBLICATIONS

International Preliminary Report on Patentability for the International Patent Application No. PCT/US2018/048094, dated Mar. 12, 2020, 6 pages.

* cited by examiner

DEVICES AND METHODS TO ACCESS A TARGET WITHIN THE BODY

CROSS REFERENCE TO RELATED APPLICATIONS

This application is a continuation of and claims the benefit of the earlier filing date of U.S. patent application Ser. No. 16/640,566, filed on Feb. 20, 2020, and issued as U.S. Pat. No. 11,452,575 on Sep. 27, 2022, and which was a 371 U.S. National Stage of PCT Application No. PCT/US18/48094, filed Aug. 27, 2018, which claimed the benefit of priority under 35 U.S.C. § 119 to U.S. Provisional Patent Application Ser. No. 62/551,121, filed on Aug. 28, 2017, all of which disclosures are hereby incorporated by reference herein in their entireties and for all purposes.

FIELD

The present disclosure relates generally to the field of medical devices and establishing access to a target within the body, such as placing an access needle into a renal capsule in the human body. In particular, the present disclosure relates to medical devices and methods for accurately and efficiently performing a percutaneous nephrolithotomy (PCNL) procedure, while minimizing exposure of the medical professional to harmful radiation. Various medical devices relating to establishing access to a target within the body are disclosed in U.S. Provisional Application Ser. No. 62,551,120, filed Aug. 28, 2017, entitled "Devices and Methods to Access a Target Within the Body," the entire contents of which are hereby incorporated by reference in their entirety for all purposes.

BACKGROUND

Using the kidney as a target example for establishing access, to accurately access the renal capsule during a percutaneous nephrolithotomy (PCNL) procedure, medical professionals are required to orient an access needle at the proper location and angle on the patient's skin, and then advance the access needle directly into a specific location of a calyx of the kidney and at a specific depth. To minimize their exposure to the potentially harmful fluoroscopic radiation beams required to visualize the kidney(s), medical professionals typically use tongs or forceps to grip the proximal end of the access needle as it is advanced through the patient's flank. Maintaining proper direction and/or orientation of the access needle during this step is often difficult due, at least in part, to the tendency of the access needle to bow or flex while being advanced, movement of the medical professional's hand, movement and breathing of the patient, etc.

A variety of advantageous medical outcomes may therefore be realized by the devices and/or methods of the present disclosure, which provide the combined benefits of establishing and maintaining proper access to a target within the body, e.g., needle orientation during a PCNL procedure, while minimizing the medical professional's exposure to harmful fluoroscopic radiation.

SUMMARY

In one aspect, the present disclosure relates to a medical device comprising an elongate shaft, a base may be attached to a distal end of the elongate shaft, a lumen may extend through the base and the distal end of the elongate shaft and a radiopaque ring may be disposed about a portion of an outer surface of the distal end of the elongate shaft. The radiopaque ring may be coaxial with the lumen. A distal portion of the elongate shaft, including the distal end, may be angled relative to a longitudinal axis of the elongate shaft. The base and a portion of the distal end of the elongate shaft may comprise a radiolucent material. The lumen may comprise a radiolucent silicone core. The radiolucent silicone core may be configured to receive an outer surface of an access needle. The base may permanently or removably attached to the elongate shaft. The elongate shaft may be attached to a flexible neck extending from a surface of the base. A distal portion of the elongate shaft may include a recess configured to releasably engage the flexible neck. A radiopaque coil may be disposed within the radiolucent silicone core.

In another aspect, the present disclosure relates to a medical device comprising an elongate shaft, and a base may be attached to a distal end of the elongate shaft. The base may include a housing and a ball rotationally disposed within the housing. The distal end of the elongate shaft may be attached to an outer surface of the ball. A lumen may extend through the elongate shaft and the ball. A radiopaque ring may be disposed about a portion of an outer surface of the distal end of the elongate shaft. The radiopaque ring may be coaxial with the lumen. A distal portion of the elongate shaft, including the distal end, may be angled relative to a longitudinal axis of the elongate shaft. The elongate shaft may include a release mechanism configured to move between a first and second position. The ball may rotate within the housing when the release mechanism is in the first position. The ball may not rotate within the housing when the release mechanism is in the second position. A portion of the base and a portion of the distal end of the elongate shaft may comprise a radiolucent material. The lumen may comprise a radiolucent silicone core. The radiolucent silicone core may be configured to receive an outer surface of an access needle. A radiopaque coil may be disposed within the radiolucent silicone core.

In yet another aspect, the present disclosure relates to a method, comprising positioning a medical device on or above a patient in the presence of an energy beam. The medical device may comprise an elongate shaft, a base attached to a distal end of the elongate shaft, a lumen extending through the base and the distal end of the elongate shaft and a radiopaque ring disposed about a portion of an outer surface of the distal end of the elongate shaft. The method may further comprise inserting an access needle for a target calyx of a patient's kidney within the lumen extending through the base; aligning the radiopaque ring and the access needle with the target calyx; and advancing the access needle into the target calyx.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to medical devices and methods for accessing the renal capsule during a PCNL procedure, it should be appreciated that such devices and methods may be used in a variety of medical procedures, including, for example, deep brain surgeries, tissue sampling, tumor biopsies and tissue ablation procedures, etc.

As used herein, the term "C-arm" refers to a fluoroscopic X-ray system used to perform a variety of diagnostic imaging and minimally invasive surgical procedures. For example, a C-arm may be used by a medical professional to guide an access needle to a specific anatomical location while visualizing the access needle on an X-ray screen.

As used herein, the singular forms "a." "an," and "the" are intended to include the plural forms as well, unless the context clearly indicates otherwise. It will be further understood that the terms "comprises" and/or "comprising." or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

Figure 1A:
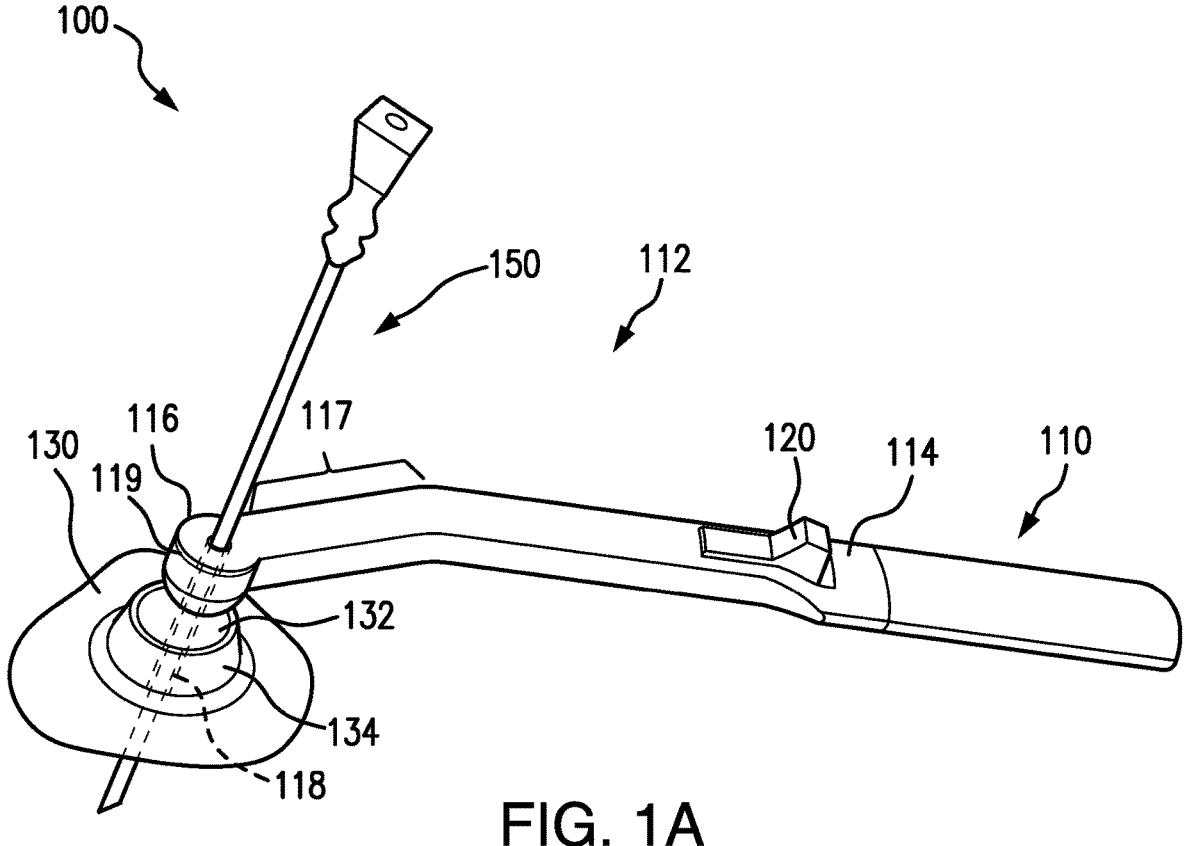
FIGS. 1A-1B provide perspective views of a needle guide, according to one embodiment of the present disclosure.
Figure 1B:
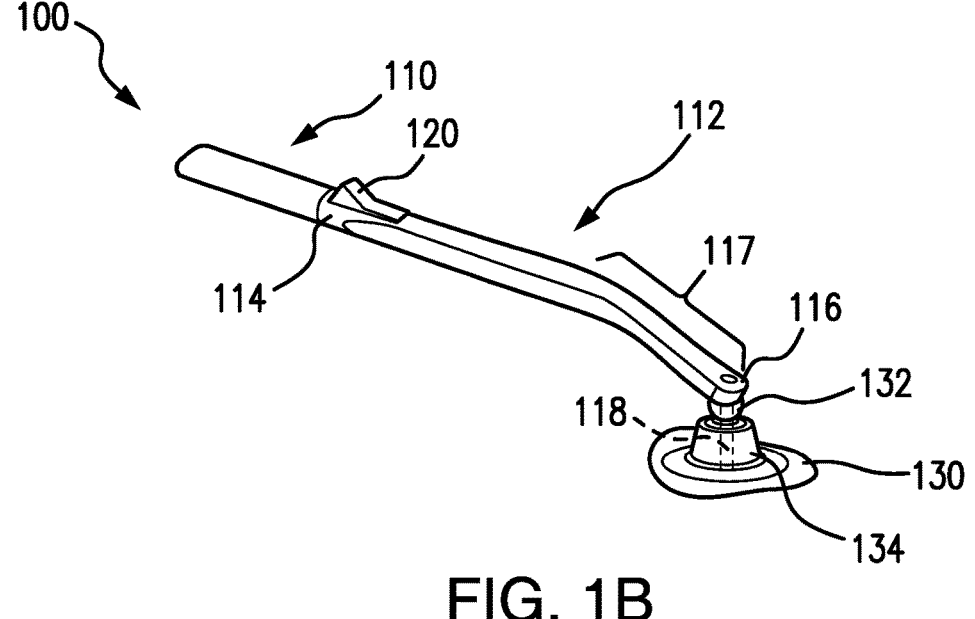

In various embodiments, the present disclosure relates to devices and methods for positioning an access needle at a target location within the human body. Referring to FIGS. 1A-1B, in one embodiment, a needle guide 100 of the present disclosure may include an elongate shaft 112 comprising a proximal end 114 and a distal end 116. The proximal end 114 of the elongate shaft 112 may be attached to a handle 110, and the distal end 116 of the elongate shaft 112 may be pivotally attached to a base 130. For example, the distal end 116 of the elongate shaft 112 may be attached to an outer surface of a corresponding ball 132 rotationally disposed within a housing 134 formed within, and extending through, an approximate center portion of the base 130. A lumen 118 may extend through both the elongate shaft 112 (e.g., at or near the distal end 116) and the ball 132. The lumen may be contiguous. In one embodiment, a portion of the lumen 118 may comprise a non-radiopaque (e.g., radiolucent) silicone core, sized and configured to grip or receive the outer circumference of an access needle 150 with sufficient force to retain a position of the access needle 150 within the base 130 when not acted upon by an external force (e.g., force exerted by a medical professional), but to allow the access needle 150 to move or slide within/through the base 130 when acted upon (e.g., retracted or extended) by an external force. A ring or band 119 comprising a radiopaque material, e.g., bismuth sulfate, metals, and/or polymers that include, or are coated or covered with, radiopaque fillers, powders, flakes, etc., may be disposed around an outer surface of the distal end 116 of the elongate shaft 112. In one embodiment, portions of the base 130, ball 132, housing 134 and/or distal end 116 of the elongate shaft 112 may be formed from or include a variety of non-radiopaque (e.g., radiolucent) materials, such that the radiopaque (RO) ring 119 may serve as bullseye through which the medical professional may visualize the radiopaque access needle (e.g., centered within the RO ring) and target calyx under fluoroscopic imaging. Alternatively, the needle guide 100 may be positioned on the patient's skin without the access needle 150 disposed within the lumen 118. Once the needle guide 100 is properly positioned on the patient's skin, the access needle 150 may be introduced into the lumen 118 and advanced to the target calyx, as discussed below.

In one embodiment, a release mechanism may be incorporated within the needle guide 100 and configured to allow the ball 132 to move between a locked and unlocked configuration within the housing 134. For example, in the locked configuration, the ball 132 may be immobilized within the housing 134, such that movement (e.g., rotating, twisting, lifting, pivoting, etc.) of the handle 110 results in corresponding movement of the base 130. In the unlocked configuration, the ball 132 may be free to move within the housing 134, e.g., with 360° of rotation in the horizontal plane and 45° of rotation in the vertical plane, without imparting any substantial movement to the base 130. As discussed below, the unlocked configuration may allow a medical professional to move the handle 110 as necessary to align the RO ring 119 and access needle 150 with a target calyx without lifting, moving or repositioning the base 130.

In one embodiment, the release mechanism may include a release lever 120 incorporated within a proximal portion of the elongate shaft 112 (e.g., near the handle 110) and connected to an actuatable member (not shown) which extends along an inner length of the elongate shaft 112. The actuatable member may include a proximal end operably attached to the release lever 120, and a distal end configured to releasably engage an inner or outer surface of the housing 134. With the release lever 120 in a first (e.g., forward) position, the actuatable member may be maintained in an extended configuration such that the distal end engages the housing 134 to prevent rotation of the ball 132 therein. With the release lever 120 moved from the first position to a second (e.g., retracted) position, the distal end of the actuatable member may not engage the housing 134, thereby allowing the ball 132 to freely rotate therein (e.g., as the handle 110 is rotated, twisted, pivoted, etc.).

In one embodiment, a distal portion 117 of the elongate shaft 112 may be bent or angled relative to the remaining portion of the elongate shaft 112. For example, the distal portion 117 may include an angle of approximately 30° to approximately 45° relative to a longitudinal axis of the elongate shaft 112. In one embodiment, the angled portion may provide an ergonomic design which allows the medical professional to more easily rotate, twist, raise, lower, pivot, or otherwise transfer force to the base 130 on or along the patient's skin, for improved stability and to establish and/or maintain proper orientation with a specific (e.g., target) calyx of the kidney, as discussed below. In various other embodiments, the base 130 may include a variety of shapes other than the shape depicted in FIGS. 1A-1B, including, for example, round, oblong, elliptical, triangular, square, rect-angular and combinations or iterations thereof.

Figure 2A:
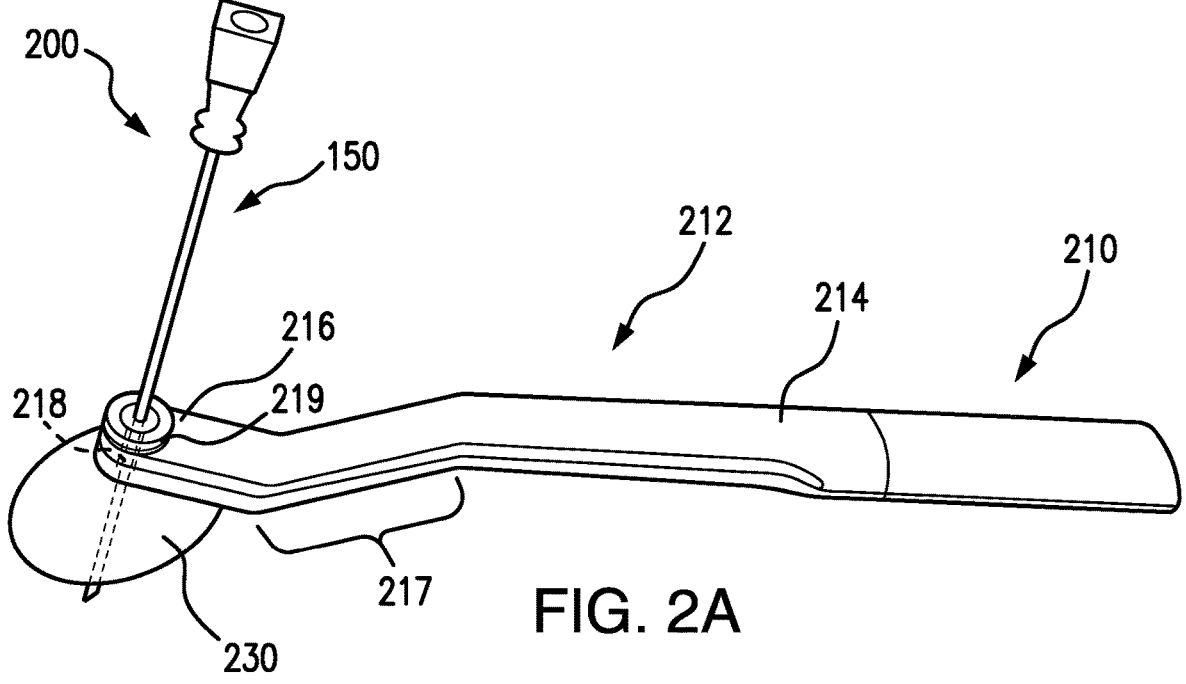
FIGS. 2A-2C provide perspective views of a needle guide, according to one embodiment of the present disclosure.
Figure 2B:
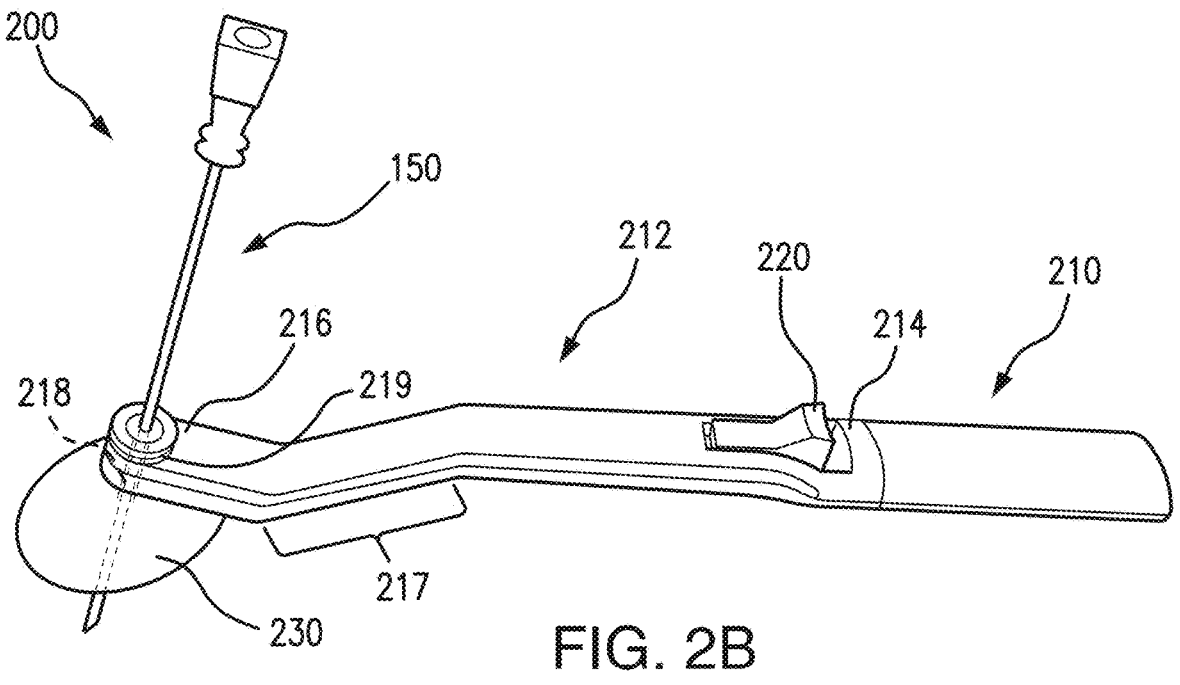
Figure 2C:
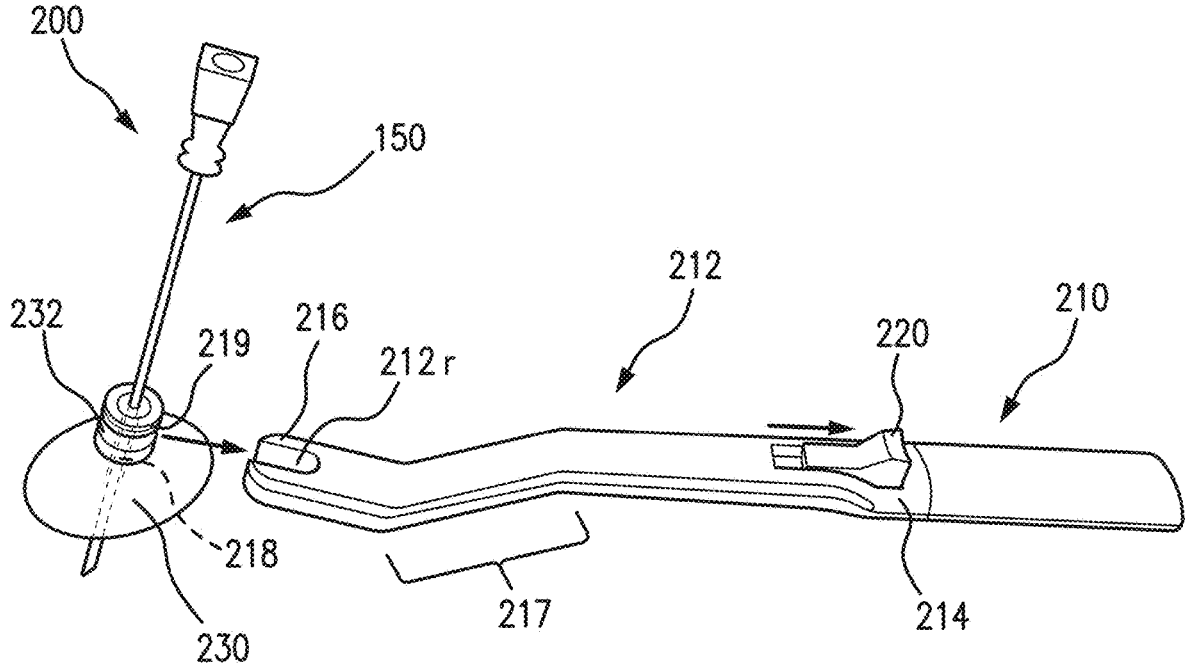

Referring to FIGS. 2A-2C, in one embodiment, a needle guide 200 of the present disclosure may include an elongate shaft 212 comprising a proximal end 214 and a distal end 216. The proximal end 214 of the elongate shaft 212 may be attached to a handle 210, and the distal end 216 of the elongate shaft 212 may be attached to a base 230. The base 230 may include a neck 232 (FIG. 2C) extending from an outer surface thereof. A lumen 218 may extend through the elongate shaft 212 (e.g., at or near the distal end 216), the neck 232 and an approximate midpoint of the base 230. The lumen may contiguous. In one embodiment, the lumen 218 may comprise a radiolucent silicone core, sized and config-ured to grip or receive the outer circumference of an access needle 150 with sufficient force to retain a position of the access needle 150 within the base 230 when not acted upon by an external force (e.g., force exerted by a medical professional), but to allow the access needle 150 to move or slide within/through the base 230 when acted upon (e.g., retracted or extended) by an external force. A ring or band 219 comprising a radiopaque material, e.g., bismuth sulfate, metals, and/or polymers that include, or are coated or covered with, radiopaque fillers, powders, flakes etc., may be disposed around portions of an outer surface of the distal end 216 of the elongate shaft 212. In one embodiment, portions of the base 230, neck 232 and/or distal end 216 of the elongate shaft 212 may be formed from or include a variety of non-radiopaque (e.g., radiolucent) materials, such that the radiopaque (RO) ring 219 may serve as bullseye through which the medical professional may visualize the radiopaque access needle (e.g., centered within the RO ring) and target calyx under fluoroscopic imaging.

In one embodiment, at least a portion of the neck 232 may comprise a suitably flexible, malleable or deformable mate-rial (e.g., silicone, rubber, flexible polymers, etc.) configured to allow a medical professional to manipulate (e.g., rotate, raise, lower, twist etc.) the handle 210 as necessary to align the RO ring 219 and access needle 150 with a target calyx without imparting or causing any, or substantially any, corresponding movement of the base 230.

In one embodiment, the distal end 216 of the elongate shaft 212 may include a recessed portion 212r (FIG. 2C) configured to releasably engage a portion of an outer surface of the neck 232. A release mechanism (FIGS. 2B-2C) may be incorporated within the handle 210, or proximal portion of the elongate shaft 212, and configured to move a securing member (not shown) between a locked and unlocked con-figuration within the recessed portion 219. In one embodi-ment, the release mechanism may include a release lever 220 incorporated within a proximal portion of the elongate shaft 212 (e.g., near the handle 210) and connected to an actu-atable member (not shown) which extends along an inner length of the elongate shaft 212 into the recessed portion 212r. The actuatable member may include a proximal end operably attached to the release lever 220, and a distal end configured to releasably engage at least a portion of the outer surface of the neck 232 within the recessed portion 212r. With the release lever 220 in a first (e.g., forward) position, the actuatable member may be maintained in an extended configuration such that the distal end engages the neck 232 of base 230. With the release lever 220 moved from the first position to a second (e.g., retracted) position, the distal end of the actuator does not engage the neck 232, thereby allowing the elongate shaft 212 to be separated from the base 230. In various embodiments, the base 230 may be disen-gaged from the distal end 216 of the elongate shaft 212 after the access needle 150 is properly positioned within the target calyx to reduce the amount of force exerted on the patient and/or minimize the likelihood of accidental contact with the elongate shaft 212 and/or handle 210 imparting trauma to the target calyx. If desired, the base 230 may be re-engaged with the distal end 216 of the elongate shaft 212 by re-engaging the distal end of the actuator with the neck 232 while the release lever 220 is in the second (e.g., retracted) position, and then moving the release lever 220 to the first (e.g., forward) position, such that the actuatable member is maintained in the extended configuration and the distal end once again engages the neck 232 of base 230.

In one embodiment, a distal portion 217 of the elongate shaft 212 may be bent or angled relative to the remaining portion of the elongate shaft 212. For example, the distal portion 217 may include an angle of approximately 30° to approximately 45° relative to a longitudinal axis of the elongate shaft 212. In one embodiment, the angled portion may provide an ergonomic design which allows the medical professional to more easily rotate, twist, pivot, or otherwise transfer force to the base 230 on or along the patient's skin, to establish and/or maintain proper orientation with a target calyx. In various other embodiments, the base 230 may include a variety of shapes other than the oblong shape depicted in FIGS. 2A-2C, including, for example, round, elliptical, triangular, square, rectangular and combinations or iterations thereof.

Figures 3A, 3B:
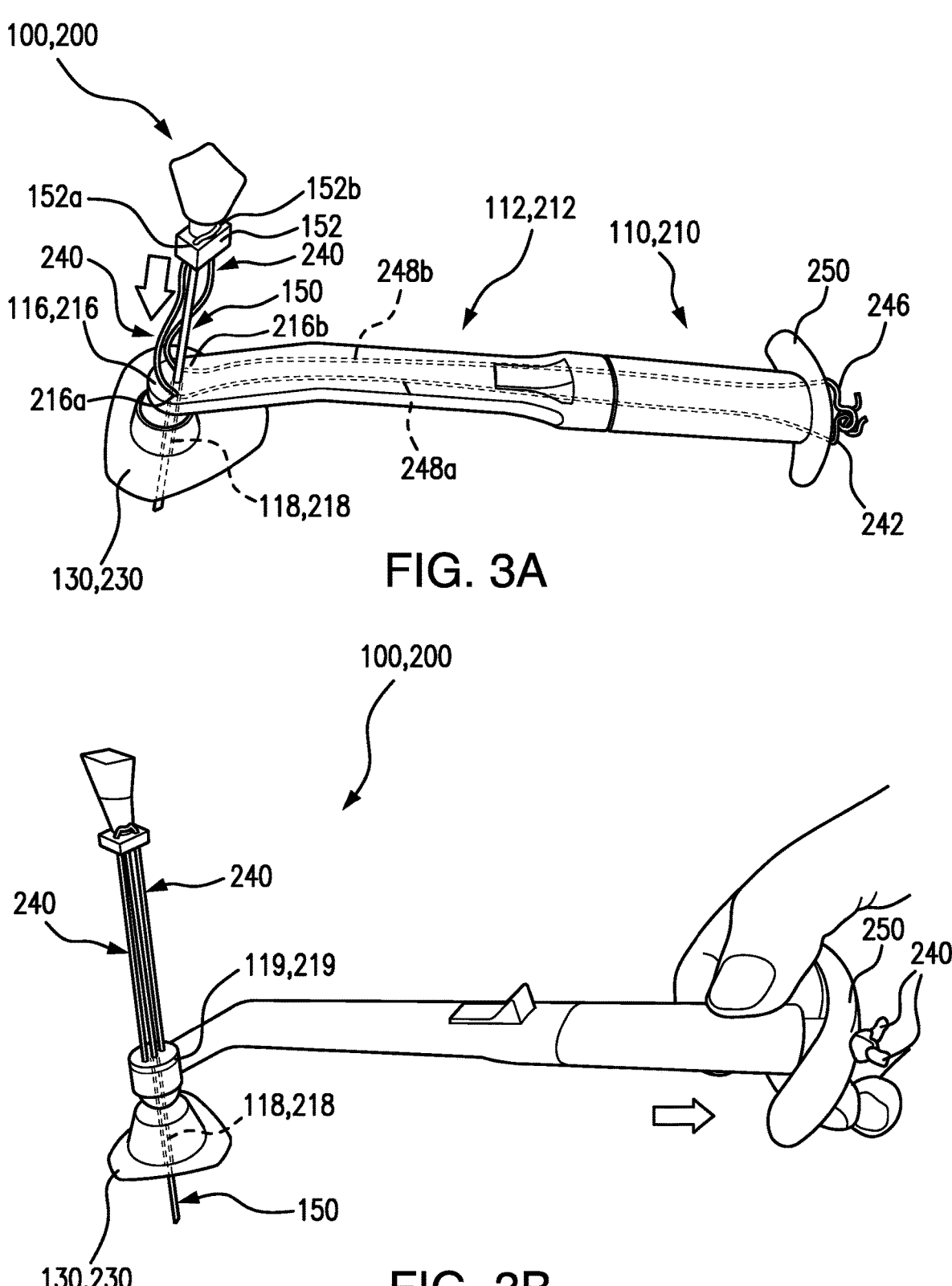
FIGS. 3A-3D provide perspective views of a needle guide, according to one embodiment of the present disclosure.
Figure 3C:
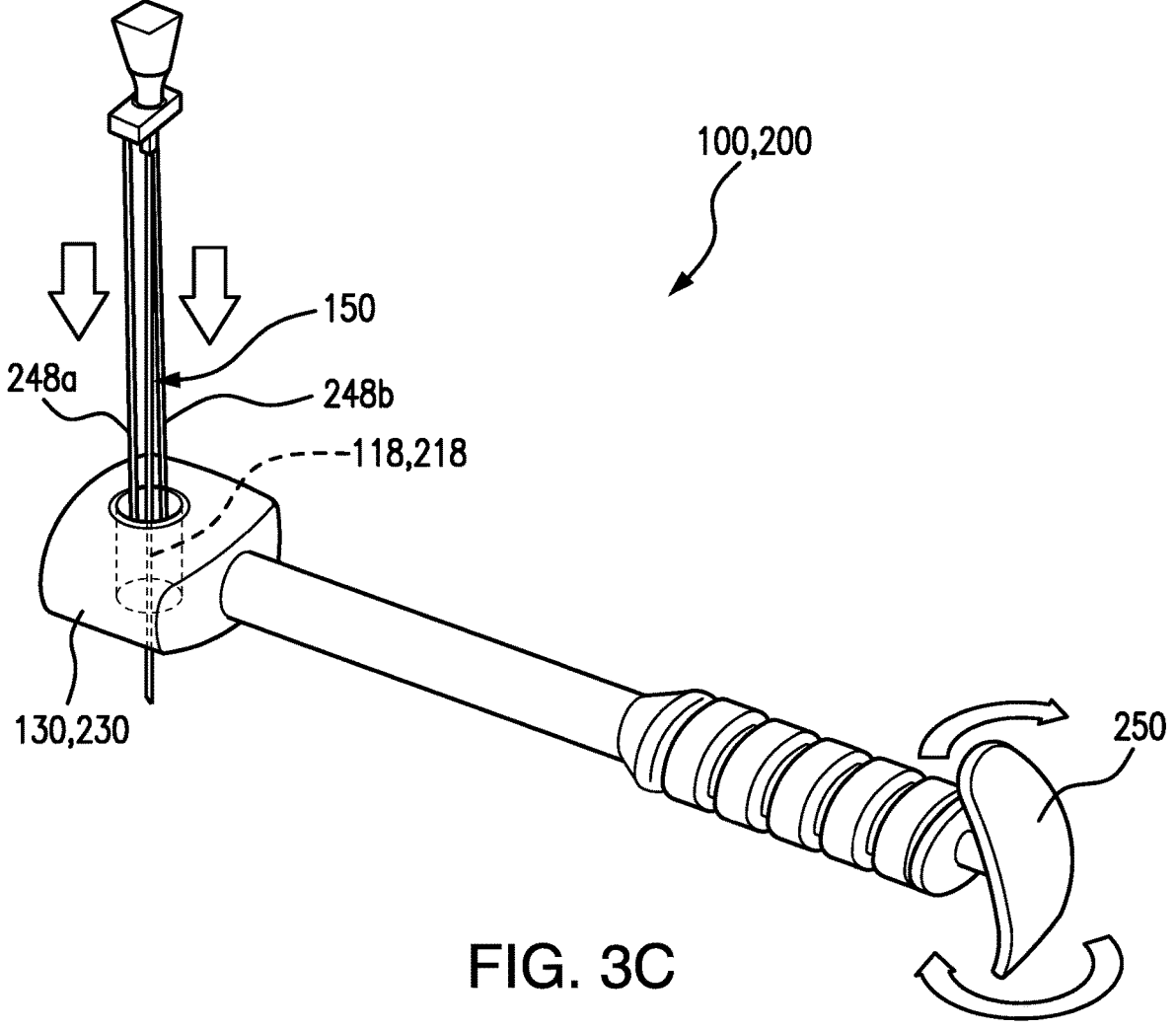

Referring to FIGS. 3A-3D, in one embodiment, a needle guide 100, 200 of the present disclosure may further include a filament 240 (e.g., suture, wire, string, etc.) which forms a loop extending through at least a portion of the elongate shaft 112, 212 and configured to effectuate movement of an access needle 150 disposed within the lumen 118, 218 of the respective base 130, 230. Referring to FIG. 3A, in one embodiment, the filament 240 may include first and second ends 242, 246 attached (e.g., glued, tied, etc.) to an actu-atable member 250 (e.g., knob, grip, etc.) positioned at or near a proximal end of the handle 110, 210. A first portion 248a of the loop may extend through the handle 110, 210 and elongate shaft 112, 212 and pass through a first opening 216a located at or near the distal end 116, 216 of the elongate shaft 112, 212. The first portion 248a of the loop may further extend from the elongate shaft 112, 212 to pass through a first opening 152a formed within a platform 152 disposed on or about a proximal portion of the access needle 150. A second portion 248b of the loop may pass through a second opening 152b formed within the platform 152 (e.g., adjacent to, or in the vicinity of, the first opening 152a) and further extend through a second opening 216b located at or near the distal end 116, 216 of the elongate shaft 112, 212 (e.g., adjacent to, or in the vicinity of, first opening 216a). The second portion 248b of the loop may further extend through the elongate shaft 112, 212 and handle 110, 210 to the actuatable member 250.

Figure 3D:
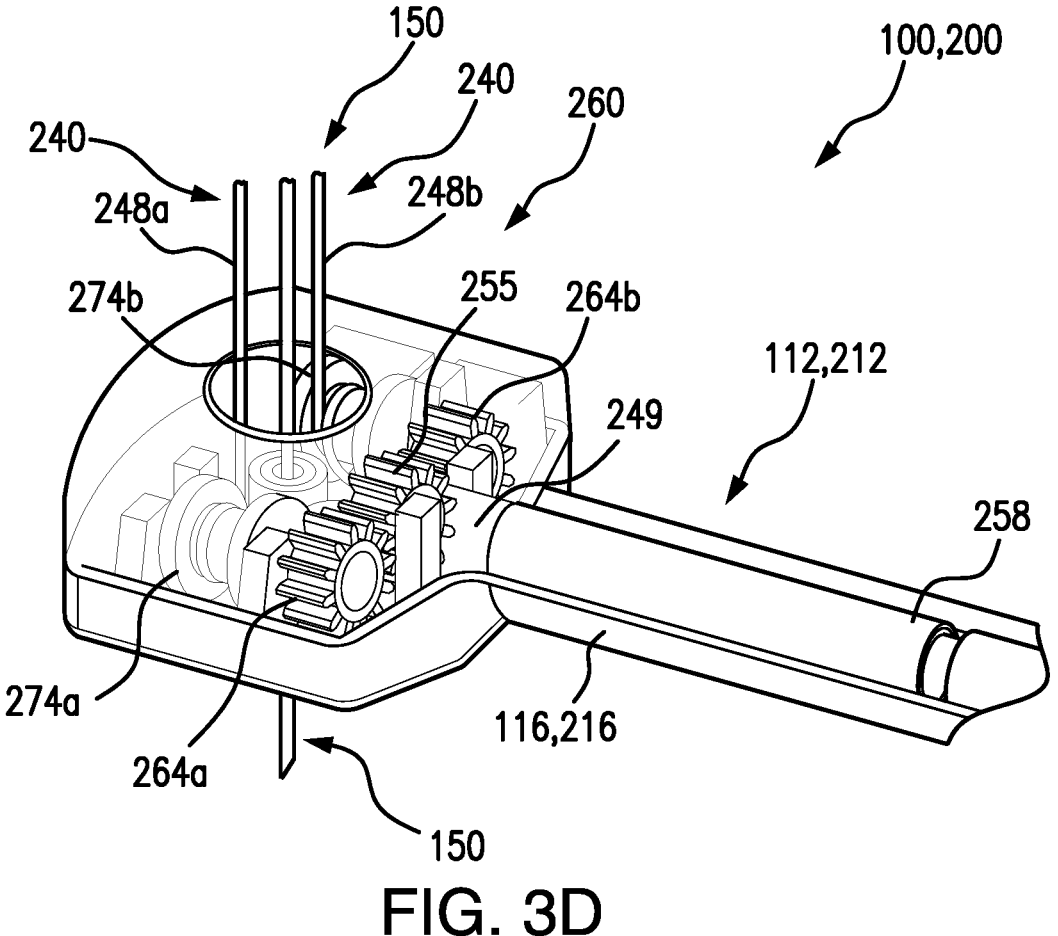

Referring to FIG. 3B, in one embodiment, a medical professional may retract/pull the actuatable member 250, and filament 240 attached thereto, proximally away from the handle 110, 210 to draw the access needle 150 through the lumen 118, 218 of the respective base 130, 230. Alterna-tively, referring to FIG. 3C, in one embodiment a medical professional may rotate the actuatable member 250 in a clockwise or counterclockwise direction to gradually shorten a length of the first and second portion 248a, 248b of the filament and draw the access needle 150 through the lumen 118, 218 of the respective base 130, 230. Referring to FIG. 3D, in one embodiment, the needle guide 100, 200 may further include a housing 260 attached to, or extending from, the distal end 116, 216 of the elongate shaft 112, 212 and in contact with an upper surface of the base (not shown). The housing 260 may include one or more gears 264a, 264b operably connected to an actuation rod 258 extending from the actuatable member (not shown) through the elongate shaft 112, 212. A distal end 249 of the actuation rod 258 may include a gear 255 configured to engage corresponding gears 264a, 264b. As the actuatable member is rotated, the corresponding rotation of the actuation rod 258 may impart rotation from the gear 255 to gears 264a. 264b. Each of the gears 264a, 264b may be attached to a corresponding roller 274a, 274b, each of which may include an outer surface in contact with a respective first or second portion 248a, 248b of filament 240. As rotation from gears 264a, 264b is imparted to respective rollers 274a, 274b, the first portion 248a of the filament may wrap around roller 274a, and the second portion 248b of the filament may wrap around roller 274b, to draw the access needle 150 through the lumen (not shown) of the respective base (not shown).

In various embodiments, the gear mechanism of FIG. 3D may provide a mechanical advantage to allow a medical professional to more easily advance the access needle 150 to a target site within the patient. In addition, or alternatively, the gear mechanism may be configured such that each rotation, or partial rotation, of the actuatable member may advance the access needle 150 through the base 130, 230 a predetermined distance to allow the medical professional to incrementally and precisely advance/ratchet the access needle into the target calyx. In one embodiment, a motor (e.g., a variable step motor) may be incorporated within the housing or elongate shaft to effect rotation of the actuation rod, gears and rollers.

Figure 4:
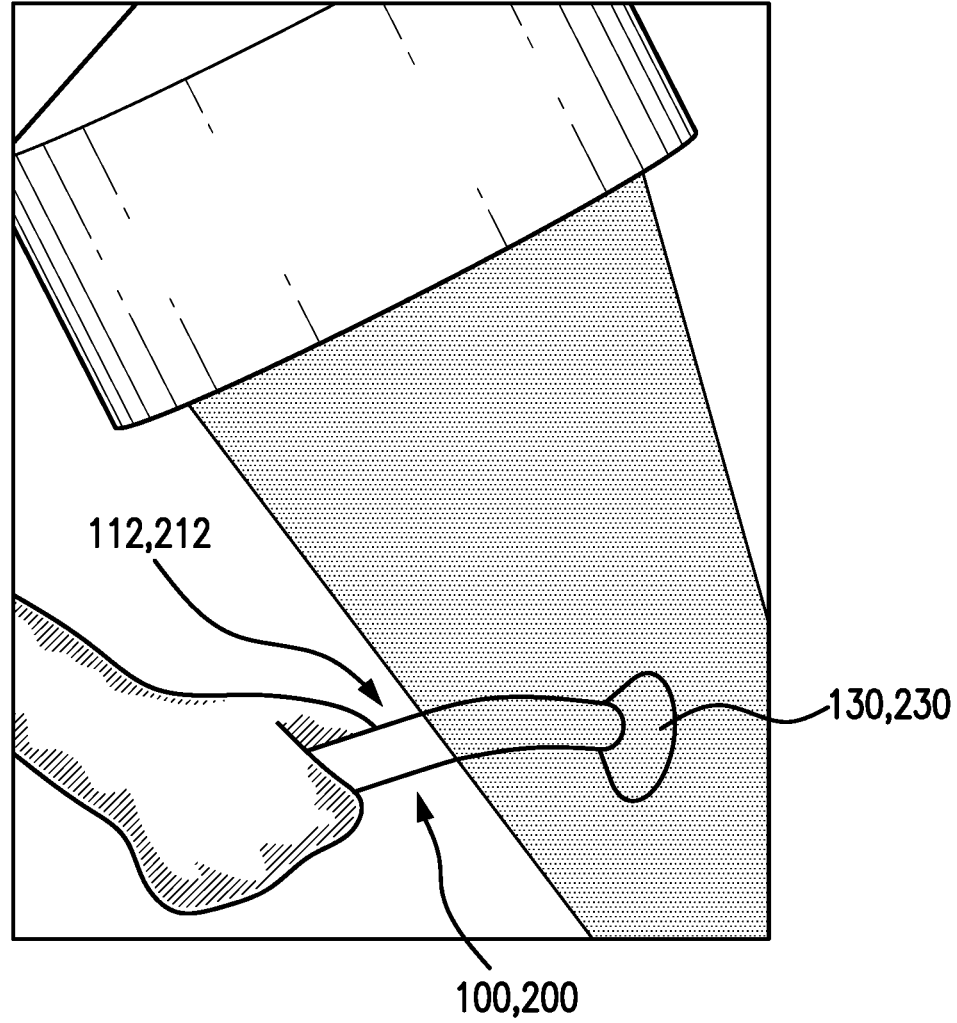
FIG. 4 provides a schematic illustration of a needle guide in use during a medical procedure, according to one embodiment of the present disclosure.

Referring to FIG. 4, in various embodiments, a needle guide 100, 200 of the present disclosure may include an elongate shaft 112, 212 with a sufficient length (e.g., at least 10 inches or more, at least 15 inches or more, at least 20 inches or more) to allow a medical professional to position the base 130, 230 at a desired location on a patient's skin without exposing a medical professional's hand(s) or arm(s) to a radiation beam emitted from a fluoroscope during a medical procedure. In addition, or alternatively, the filament 240 of FIGS. 3A-3D may also allow the medical professional to accurately and precisely advance the access needle to a target location and depth within the patient without exposing their arms or hands to the radiation beam.

Although needle guides 100, 200 of the present disclosure are generally disclosed as being configured to align respective lumens 118, 218 to match the corresponding angle of a C-arm (e.g., at an angle of a C-arm 30 degree lateral, 0 degree caudal), in various embodiments, the lumens may be configured to match or accommodate a variety of C-arm angles (e.g., in a range between 0° and 50°).

Although the RO ring 119, 219 of the present disclosure is generally depicted as extending around an outer surface of the distal end 116, 216 of the elongate shaft 112, 212, in various embodiments the RO ring may be integrally formed on or within the distal end 116, 216 of the elongate shaft 112, 212 (e.g., during the molding process). In various other embodiments, the RO ring 119, 219 may be coaxial with the lumen 118, 218. In various other embodiments, a needle guide 100, 200 of the present disclosure may include multiple RO rings or bands spaced apart along, around and/or coaxial with the lumen 118, 218 to allow a medical professional to align the multiple rings with each other and with another reference point (e.g., the access needle, target calyx, etc.) under fluoroscopic imaging In addition to the RO ring, or as an alternative to the RO ring, in various embodiments the silicone core defining the lumen 118, 218 may further include a radiopaque coil disposed therein, to allow the medical professional to align the radiopaque access needle 150 with the target calyx, as discussed above.

In one embodiment, the handle 110, 210 of needle guide 100, 200 may be permanently or releasably attached to the elongate shaft 112, 212. Although elongate shafts 112, 212 of the present disclosure are generally disclosed as including a bent/angled distal portion 117, 217, in various embodiments, the elongate shaft 112, 212 may be substantially straight along an entire longitudinal axis thereof, and with the lumen 118, 218 extending through the distal portion at an angle, e.g., an angle of approximately 30° to approximately 45° relative to a longitudinal axis of the elongate shaft 112. In various embodiments, base 130, 230 may include a variety of soft and/or flexible polymeric materials configured to conform to a surface which the base in pressed against, including, for example, a patient's skin.

In one embodiment, in use and by way of example, a medical professional may position a needle guide 100 of the present disclosure on or above a patient's flank (e.g., between the eleventh and twelfth ribs) in the presence of a beam of X-ray energy emitted from a C-arm at position C-arm 30,0. Once the puncture site on the patient's flank is established, the medical professional may move the release lever 120 from the first to second position to unlock the ball 132, and incline the handle 110 while maintaining the base 130 in contact with the patient's skin. The handle 110 may be moved as necessary until the bullseye (e.g., formed by the access needle 150 centered within the RO ring 119) aligns with the target calyx on the fluoroscopic image. With the proper angle to the needle trajectory established, the C-arm may be moved to position C-arm 0,0 to establish the distance between the patient's skin and the target calyx. The medical professional may then advance the access needle the required distance into the target calyx.

In another embodiment, in use and by way of example, a medical professional may position a needle guide 200 of the present disclosure on or above a patient's flank (e.g., between the eleventh and twelfth ribs) in the presence of a beam of X-ray energy emitted from a C-arm at position C-arm 30,0. Once the puncture site on the patient's flank is established, the medical professional may move the handle 210 while maintaining the base 230 in contact with the patient's skin. The handle 210 may be moved as necessary until the bullseye (e.g., formed by the access needle 150 centered within the RO ring 219) aligns with the target calyx on the fluoroscopic image. With the proper angle to the needle trajectory established, the C-arm may be moved to position C-arm 0,0 to establish the distance between the patient's skin and the target calyx. The medical professional may then advance the access needle the required distance into the target calyx.

Proper placement of the access needle within the target calyx may be confirmed by urine exiting through the needle lumen after the stylet has been removed. A guidewire may be inserted through the access needle into the target calyx, and the access needle removed from the patient. A dilator may then be introduced over the guidewire and positioned within the first calyx. A sheath may then be introduced over the dilator to allow a medical professional to introduce medial tools, e.g., to remove obstructions, including kidney stones.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device configured for guiding a needle, said device comprising:
   a base;
   a neck extending from said base; and
   an elongate shaft having a distal end couplable with said neck, a proximal end, and an elongated extent therebetween;
   wherein:
   a lumen extends through said elongate shaft, said neck, and said base; and
   said neck is flexible and configured to allow manipulation thereof by said elongate shaft when coupled with said neck to manipulate said neck to adjust and to align the lumen with a target within a patient's body without moving said base.

2. The medical device of claim 1, wherein said neck is formed of a malleable or deformable material.

3. The medical device of claim 2, wherein said neck is formed of a material selected from the group consisting of: silicone, rubber, and flexible polymers.

4. The medical device of claim 1, wherein said elongate shaft extends laterally away from said base and is rotatable, twistable, raisable, lowerable, and pivotable to adjust the orientation of the lumen.

5. The medical device of claim 1, wherein the lumen extends through the distal end of said elongate shaft in a direction transverse to the elongated extent of said elongate shaft.

6. The medical device of claim 1, wherein the distal end of said elongate shaft includes a recessed portion configured to releasably engage a portion of an outer surface of said neck.

7. The medical device of claim 6, further comprising a release mechanism movable between a first position in which the distal end of said elongate shaft is locked with respect to said neck and a second position in which said elongate shaft is separable from said neck.

8. The medical device of claim 1, wherein the lumen comprises a radiolucent core.

9. The medical device of claim 1, wherein the lumen is sized and configured to grip an outer circumference of the needle to retain a position of the needle within said base when not acted upon by an external force.

10. The medical device of claim 9, wherein the lumen is sized and configured to allow the needle to move or slide with respect to said base when acted upon by an external force.

11. The medical device of claim 1, wherein a radiopaque material is disposed around portions of an outer surface of said elongate shaft.

12. The medical device of claim 11, wherein a portion of at least one of said elongate shaft, said base, or said neck is formed from a non-radiopaque material.

13. The medical device of claim 11, wherein said radiopaque material is disposed around outer portions of an outer surface of the distal end of said elongate shaft.

14. A system for gaining access into a patient's body, said system comprising:
   a base;
   a neck extending from an outer surface of said base;
   an elongate shaft having a distal end couplable with said neck, a proximal end, and an elongated extent therebetween; and
   an access needle;
   wherein:
   a lumen, sized to receive an outer circumference of said access needle, extends through said elongate shaft, said neck, and said base;
   said neck is flexible and configured to allow manipulation thereof by movement of said elongate shaft when coupled with said neck to manipulate said neck to adjust and to align the lumen and said access needle with a target within the patient's body without moving said base.

15. The system of claim 14, wherein said access needle is radiopaque.

16. The system of claim 14, wherein the lumen comprises a radiolucent core.

17. The system of claim 14, wherein the lumen is sized and configured to grip the outer circumference of said access needle to retain a position of said access needle within said base when not acted upon by an external force.

18. The system of claim 14, wherein the lumen is sized and configured to allow said access needle to move or slide with respect to said base when acted upon by an external force.

19. A method of accessing a target within a patient's body, said method comprising: grasping a handle formed on a proximal end of an elongate shaft, a distal end of the elongate shaft being engaged with a flexible neck extending from an outer surface of a base; extending a needle through a lumen extending through the distal end of the elongate shaft, the flexible neck, and the base; manipulating the elongate shaft to flex the flexible neck to adjust and to align the lumen and to adjust and to align the position of the needle with respect to the target within the patient without moving the base; and advancing the needle into the patient to the target.

20. The method of claim 19, comprising releasing the handle from the neck.

* * * * *